(12) United States Patent
Khassanov et al.

(10) Patent No.: US 9,817,998 B2
(45) Date of Patent: *Nov. 14, 2017

(54) SECURE ACCESS TO INDIVIDUAL INFORMATION

(71) Applicant: VYRTY Corporation, Issaquah, WA (US)

(72) Inventors: Raif Khassanov, Sammamish, WA (US); Eugene Luskin, Issaquah, WA (US); Yakov P. Grinberg, Sammamish, WA (US); Eugene Kolker, Kirkland, WA (US)

(73) Assignee: VYRTY Corporation, Issaquah, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,220

(22) Filed: Feb. 16, 2017

(65) Prior Publication Data

US 2017/0161518 A1    Jun. 8, 2017

Related U.S. Application Data

(63) Continuation of application No. 14/873,107, filed on Oct. 1, 2015, now Pat. No. 9,613,226.

(60) Provisional application No. 62/058,107, filed on Oct. 1, 2014, provisional application No. 62/066,866, filed on Oct. 21, 2014, provisional application No. 62/110,613, filed on Feb. 2, 2015, provisional application No. 62/134,490, filed on Mar. 17, 2015, (Continued)

(51) Int. Cl.
*G06F 21/62* (2013.01)
*G06F 19/00* (2011.01)
*H04L 29/06* (2006.01)
*G06F 21/60* (2013.01)

(52) U.S. Cl.
CPC ........ *G06F 21/6245* (2013.01); *G06F 19/322* (2013.01); *G06F 21/602* (2013.01); *H04L 63/0428* (2013.01); *H04L 63/0853* (2013.01)

(58) Field of Classification Search
CPC .................................................. G06F 21/6245
See application file for complete search history.

(56) References Cited

U.S. PATENT DOCUMENTS

| 6,944,767 B1 * | 9/2005 | Judson .................. G06Q 10/02 705/3 |
| 7,424,437 B2 * | 9/2008 | Maus .................. A61B 5/0002 422/68.1 |

(Continued)

OTHER PUBLICATIONS

Löhr et al.; Securing the e-health cloud; Published in: Proceeding IHI '10 Proceedings of the 1st ACM International Health Informatics Symposium; pp. 220-229; Arlington, Virginia, USA—Nov. 11-12, 2010; ACM Digital Library.*

(Continued)

*Primary Examiner* — Bradley Holder
(74) *Attorney, Agent, or Firm* — Perkins Coie LLP

(57) ABSTRACT

A facility for accessing information relating to a person is described. In a reader device, the facility accesses first credentials stored in a first storage device, second credentials stored in a second storage device, and third credentials stored in the reader device. In the reader device, the facility uses a combination of the first credentials, second credentials, and third credentials to decrypt information relating to the person stored in the first storage device.

26 Claims, 14 Drawing Sheets

Related U.S. Application Data provisional application No. 62/154,612, filed on Apr. 29, 2015.

(56) References Cited

U.S. PATENT DOCUMENTS

| | | | |
|---|---|---|---|
| 9,613,226 B2 | 4/2017 | Khassanov et al. | |
| 2003/0040940 A1* | 2/2003 | Nehammer | G06F 3/08 705/3 |
| 2003/0074564 A1* | 4/2003 | Peterson | G06F 19/322 713/182 |
| 2005/0055560 A1 | 3/2005 | Kendon | |
| 2005/0086497 A1 | 4/2005 | Nakayama et al. | |
| 2005/0195975 A1* | 9/2005 | Kawakita | H04L 9/0822 380/30 |
| 2005/0237776 A1* | 10/2005 | Gropper | G06F 17/5036 365/1 |
| 2006/0085347 A1* | 4/2006 | Yiachos | G06F 19/322 705/51 |
| 2007/0006322 A1 | 1/2007 | Karimzadeh et al. | |
| 2008/0071543 A1* | 3/2008 | Jarvis | G04G 15/006 704/270 |
| 2009/0112627 A1* | 4/2009 | Berkman | G06Q 50/22 705/3 |
| 2009/0204433 A1* | 8/2009 | Darian | G06Q 50/22 705/3 |
| 2010/0030690 A1* | 2/2010 | Herlitz | G06F 19/322 705/50 |
| 2010/0122083 A1* | 5/2010 | Gim | G06F 21/6245 713/162 |
| 2013/0200999 A1* | 8/2013 | Spodak | G05B 1/01 340/5.65 |
| 2016/0232306 A1* | 8/2016 | Achan | G06Q 50/22 |

OTHER PUBLICATIONS

Hall et al.; Enabling remote access to personal electronic medical records; Published in: IEEE Engineering in Medicine and Biology Magazine ( vol. 22, Issue: 3, May-Jun. 2003 ); pp. 133-139; Date of Publication: Jul. 22, 2003; IEEE Xplore.*

International Search Report and Written Opinion for Application No. PCT/US2015/053612; Applicant: VYRTY Corporation; dated Jan. 21, 2016; 21 pages.

Lohr et al., Securing the E-Health Cloud, IHI'10, Nov. 11-12, 2010, Arlington, Virginia, © 2010 ACM, pp. 220-229, 10 pages.

Hall et al., Enabling remote access to personal electronic medical records; Published in: IEEE Engineering in Medicine and Biology Magazine (vol. 22, Issue: 3, May-Jun. 2003), pp. 133-139, published Jul. 22, 2003, IEEE Xplore.

Notice of Allowance received from the U.S. Patent Office for U.S. Appl. No. 14/873,107, dated Jan. 4, 2017, 22 pages.

* cited by examiner

SECURE ACCESS TO INDIVIDUAL INFORMATION

CROSS-REFERENCE TO RELATED APPLICATION(S)

This application is a continuation of U.S. patent application Ser. No. 14/873,107 filed Oct. 1, 2015, now U.S. Pat. No. 9,613,226, which application claims priority to and the benefit of the following applications, each of which is hereby incorporated by reference in its entirety: U.S. Provisional Application No. 62/154,612 filed Apr. 29, 2015 and titled SECURE ACCESS TO INDIVIDUAL INFORMATION; U.S. Provisional Application No. 62/134,490 filed Mar. 17, 2015 and titled SECURE ACCESS TO INDIVIDUAL INFORMATION; U.S. Provisional Application No. 62/058,107, filed on Oct. 1, 2014, and titled METHOD AND APPARATUS FOR SECURED DATA STORAGE, OFFLINE DATA EXCHANGE AND GOVERNED PROTECTED DATA ACCESS; U.S. Provisional Application No. 62/066,866, filed on Oct. 21, 2014 and titled METHOD AND APPARATUS FOR ENCRYPTED OFFLINE DATA STORAGE, PROTECTED ONLINE BACKUP AND SECURED DATA PROCESSING; and U.S. Provisional Application No. 62/110,613 filed Feb. 2, 2015 and titled METHOD AND APPARATUS FOR PROTECTED OFFLINE DATA STORAGE AND SECURE RECORDS COMPLETION AND UPDATES. In cases where material incorporated herein by reference conflicts with the present disclosure, the present disclosure controls.

BACKGROUND

Various kinds of services performed with respect to individuals rely on information about the individual. For example, medical services provided to a patient often rely on information about the patient including innate patient attributes such as date of birth, weight, and height; results of tests such as blood pressure, pulse, blood panels, and radiological studies; diagnostic and interventional histories; and health insurance information. In some contexts, the above is referred to as "patient health information." Financial services provided to a person often rely on information about the person such as Social Security number and other identifying information, credit score, employment history, and account numbers and balances. National border regulation services performed with respect to travelers often rely on information about the traveler such as identifying information, citizenship and residency status, international travel history, and photographs.

For many of these kinds of services, the advent of cloud-based storage has been accompanied by techniques for storing the corresponding individual information in the cloud, often in connection with some kind of security technique designed to reduce the risk of unauthorized access to the information. For example, cloud-based electronic medical record systems seek to store patient information on Internet-connected storage devices, such that medical service providers in a variety of locations can access the patient's electronic medical record via the Internet.

DETAILED DESCRIPTION

Figure 1:
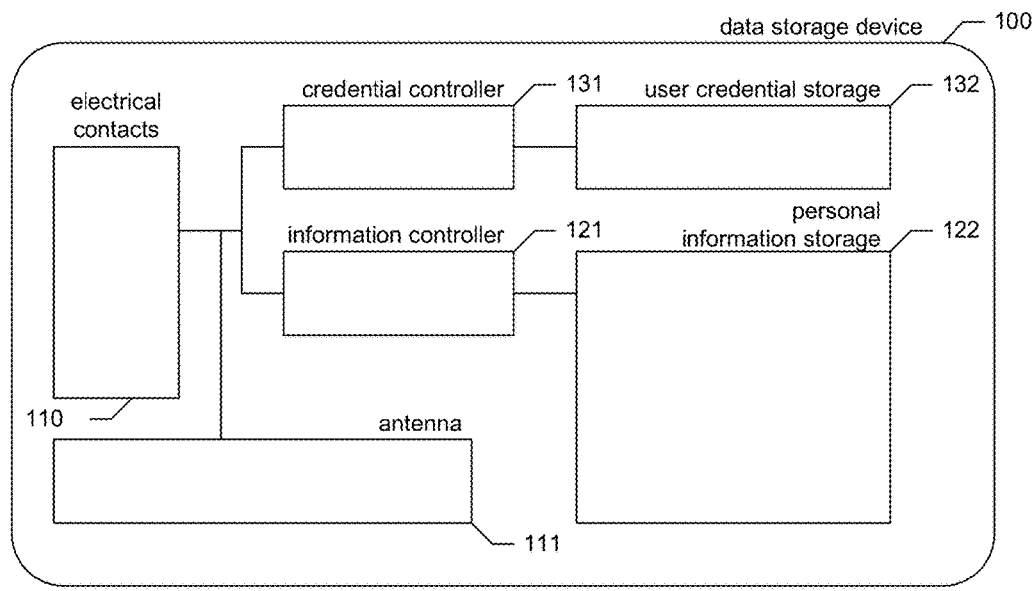
FIG. 1 is a device diagram showing components included in a data storage device used by the facility in some embodiments.

The inventors have recognized that the sorts of detailed individual information used in performing many kinds of services with respect to individuals can have significant value to data thieves, for eventual use in identity theft, blackmail, fraud, insider trading, marketing expensive niche products and services, etc. The inventors have further recognized that such unauthorized access to and exploitation of a person's individual information can be extremely expensive or otherwise disadvantageous to the person, and/or others.

The inventors have further recognized that there are a variety of kinds of information technology exploits and attacks available to information thieves that can be effective in gaining unauthorized access to data stored on any Internet-connected storage devices, even those that implement relatively sophisticated security techniques, despite ongoing efforts to protect such stored data.

Accordingly, the inventors have concluded that individual information stored in an Internet-accessible storage device to facilitate retrieval by a service provider is vulnerable to theft by information thieves, even when sophisticated, and even state-of-the-art security techniques are used.

For these reasons, the inventors have conceived and reduced to practice a software and/or hardware facility for providing secure, geographically-diverse access to individual information ("the facility"). In some embodiments, the facility enables exchange of a patient's electronic health information between healthcare providers (doctors, physicians, nurses, testing laboratories, imaging centers, and other certified individuals) via secure media that is in possession and under control of the patient.

In some embodiments, the facility uses a portable data storage device such as a smart card or other device sized similarly to a credit card to store each user's data. Where the facility is used to store health data, for example, in some embodiments the data storage device is incorporated into each user's medical insurance card or healthcare organization membership card. In particular, a data storage device stores the user's data in encrypted form, as well as credentials for the user. In some embodiments, the user credentials are, e.g., a security certificate and/or one or more cryptographic keys. In some embodiments, these credentials for the user are originated in a physically and communicatively isolated location ("a vault") into which no network connections pass, and are copied to the user's smart card inside this vault. In some embodiments, user's individual information and the user's credentials are stored separately and/or in a manner that isolates them from each other, such as in different physical or logical storage devices contained within the smart card.

Typically, each of a number of different service providers—such as physicians, medical testing or imaging centers, etc. —are outfitted with one or more data access devices, or "readers." When the user visits a service provider, to access the user's data, the user's data storage device is inserted into a reader, along with a smart card containing credentials for a service provider ("access key storage device"). For example, at a doctor's office, the user's smart card may be inserted into a reader along with a smart card containing credentials for the doctor treating the user. In various embodiments, the reader uses various protocols to interact with the smart cards inserted into them, such as USB. In some embodiments, the reader is connected to a computer system used in the service provider's practice, such as a desktop computer system or a laptop computer system.

Based on credentials on the user's smart card, service provider credentials on the service provider's smart card, and reader credentials stored in the reader, the decrypts the encrypted data on the user's smart card and provides access to it, such as via the provider computer system. For example, a doctor can access a user's social security number, test results, treatment history, etc. Further, while both smart cards are in the reader, these credentials can be used to store on the user's smart card new or changed information on the storage device in encrypted form, such as new diagnoses, treatment plans, etc. The provider computer system can be connected directly or indirectly to a variety of devices from which this new or changed information is obtained, including provider testing devices, provider storage devices, provider input devices, etc.

In some embodiments, the data access device obtains the service provider credentials in a way other than the service provider inserting a service provider smart card into the data access device. In various such embodiments, the service provider credentials are retrieved wirelessly from an object carried by or on the service provider or their proxy, such as by a smart phone or other communications device, a name tag or other identification badge, a device worn in the manner of a watch or glasses, a tag sewn into clothing, etc. In various embodiments, such wireless communication is via, for example, WiFi, Bluetooth, NFC, RFID, infrared, etc. In some embodiments, the user's credentials are provided in one or more of these alternative manners.

In some embodiments, the data access device accesses the user's encrypted data in a manner other than reading it from a smart card inserted into the data access device. In various such embodiments, the data access device reads and writes the user's encrypted data wirelessly, such as on a smart phone or other communications device carried by the user. In some embodiments, the data access device reads and writes the user's encrypted data on an Internet server.

In some embodiments, the credentials possessed by each reader that allow the reader to decrypt the contents of the user's smart card include a revolving reader certificate. This revolving reader certificate is a basis for disabling readers that are being used improperly. In the normal course of events, a new revolving reader certificate is periodically generated and distributed to all of the readers. Each reader retains all received revolving reader certificates for use in decrypting user smart card data encrypted by a reader using whatever certificate the encrypting reader had most recently received at the time of encryption, and uses the most recent revolving reader certificate to encrypt the user smart card data. However, where it is determined that a particular reader is being used improperly, the facility can deny that reader future revolving reader certificates, making it impossible for that reader to read user smart cards whose contents were encrypted using newer revolving reader certificates.

In some embodiments, the reader is configured to connect to a service provider's computer system as a standard removable storage device as a way for the service provider's computer system to store new data on the user's smart card in encrypted form. In some embodiments, the reader is further configured to connect to a service provider's computer system as a printer, so that even service provider computer systems that are not configured to store data on removable storage devices can store data on the user's smart card.

In some embodiments, at certain points when the user's smart card is in a reader, the encrypted data stored in the user's smart card is forwarded to a backup store via a strictly one-way connection—that is, because of physical limitations of how the backup store is connected to the Internet, data can only flow towards the backup store, never away from the backup store. Where a user loses his or her smart card, the facility creates a new card; within the vault, copies the user's credentials to the new card; and, at the site of the backup store, copies to the new card the user's encrypted data from the backup store. Until the user's encrypted data from the backup store is loaded onto the new card, its separation from the user's credentials stored on the card prevents its decryption.

In some embodiments, the facility enables a service provider to store data on the user's card that is not yet available to store when the user's card is removed from the service provider's reader. While the user's card is in the service provider's reader, rather than storing substantive data, the reader stores on the user's card a very large, randomly determined session identifier. When the service provider finishes generating the data to be stored on the user's card, the service provider's reader uploads to a "completion server" a copy of the data that has been encrypted with a public key associated with the user, along with the session identifier. The next time the user's smart card is inserted in any reader, it retrieves the session identifier from the user's smart card, and uses the session identifier to retrieve the encrypted data from the completion server and store this data on the user's smart card.

In some embodiments, the facility performs certain forms of collective analysis on the individual information stored on behalf of many or all of the users. E.g., in some embodiments, the readers aggregate user data across groups of users, and contribute these aggregates to an aggregated data store. For example, an insurance company may aggregate information about its patients as a basis for discerning health and/or treatment trends among the patients.

By performing in some or all of the ways described above, the facility facilitates geographically-diverse access to each user's individual information while at the same time maintaining a high level of security for this individual information.

Several use cases outlined below illustrate aspects of the operation of the facility in some embodiments and attendant benefits.

1. A first person collapses unexpectedly and is rushed to an Emergency Room. Under significant time pressure, the physicians decide to treat this patient with drug A. If, as is typical, the patient does not carry any personal medical information with her, her doctors are unable to learn that she is taking drug B, with which drug A has negative interactions. This treatment results in worsening condition for this patient, and may result in her death. These negative outcomes are avoided where her doctors are able to access a list of the patient's current prescriptions stored among her medical information on a portable storage device carried with her.

2. A second person encounters a serious chest pain, goes to see a doctor. Because he does not have personal health records with him, he is unable to identify two medications recently prescribed for him by a cardiologist. The doctor seeks from that cardiologist the identities of the prescribed medications, but the cardiologist is vacationing in a remote location beyond communications. The doctor orders exams and tests, then diagnoses the condition, and prescribes new medications. It turns out that all the same exams and tests had been done by the cardiologist earlier, and result in exactly the same prescriptions. Had this patient been carrying his medical information on a portable storage device, the prior testing, its results, and the resulting prescriptions would all have been available to the new doctor, and a substaintial amount of effort on behalf of both the doctor and patient would have been avoided, along with significant expense.

3. A third person breaks his leg while on vacation. At an urgent care facility, he is diagnosed, using X-Rays, and is released with crutches and a CD-ROM containing the X-Ray images. A few days later, he feels sudden major pain and is quickly driven to a hospital Emergency Room. Due to rush, the patient forgets to bring the CD-ROM containing his X-Ray images. As is typical, the electronic health records system of this hospital does not exchange any information with the urgent care facility visited days earlier. The Emergency Room physicians obtain new X-Ray images, and base their treatment on them, which mirror those of the earlier X-Ray study. Here also, the effort, time, and expense of redundant testing are avoided where the results of earlier tests are stored in a portable storage device carried by the patient.

Such experiences are common among patients treated by modern healthcare providers, and can often be avoided where a patient carries personal health information with him or her in a secure form.

FIG. 1 is a device diagram showing components included in a data storage device used by the facility in some embodiments. FIG. 1 shows that, in some embodiments, the data storage device 100 is a smart card. The data storage device includes both user credential storage 132 and information storage 122. The user credential storage is storage capacity on the data storage device devoted to storing user security credentials, such as security certificates, keys, etc., that are representative of the user's authority to use the data storage device. The individual information storage contains individual information for the user, such as the user's health information, encrypted in such a way that user credentials, provider credentials, and reader credentials are all needed in order to decrypt them. A credential controller 131 controls and supervises access to the user credential storage, while an information controller 121 controls and supervises access to the individual information storage. The data storage device has one or both of electrical contacts 110 and an antenna 111 to communicate with the reader to permit the reader to access the user credentials and the individual information stored on the data storage device.

In some embodiments, one role of the data access device is to isolate the patient's card from being accessed directly. In some embodiments, the facility stores data on the card in a completely different format compared to what is presented by the data access device to service provider computer systems. This enables the data access device to validate and enforce data contracts and schemas, which ensures the integrity of the data, and removes the risk of unauthorized data to "travel" on the card.

In some embodiments, the data access device contains two independent, isolated areas—one handles encryption and security, while the other executes applications aimed and different forms of data processing. In some embodiments, everything related to security is "hardcoded," such that it cannot be changed or updated remotely. In some embodiments, parts of the data aggregation and de-identification controlling settings are "hardcoded" as well. For instance, when medical information is aggregated across patients, the facility can require that the reader only report aggregates for 10 or more patients.

Figure 2:
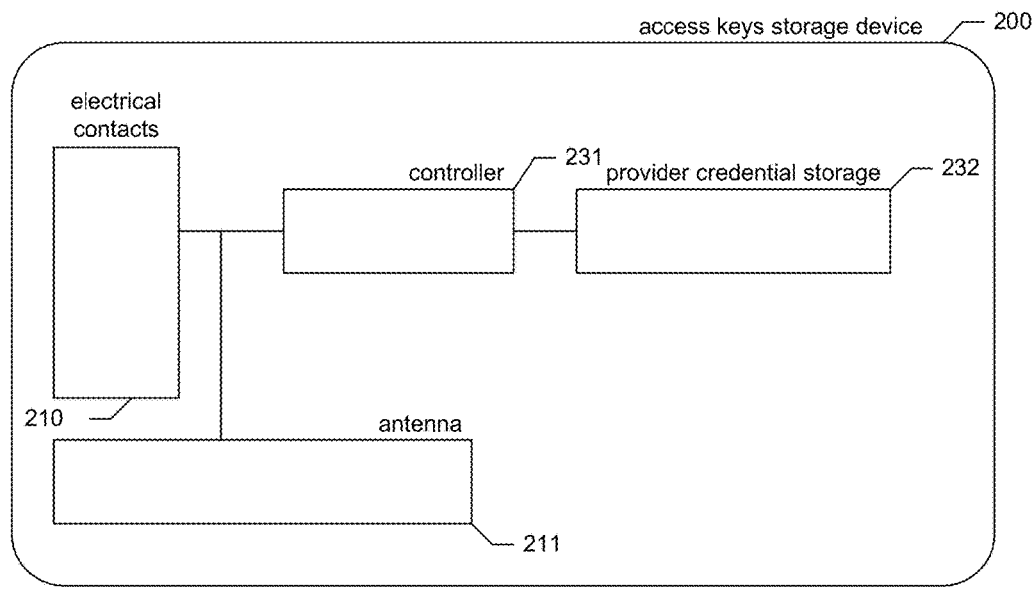
FIG. 2 is a device diagram showing an access keys storage device used by the facility in some embodiments.

FIG. 2 is a device diagram showing an access keys storage device used by the facility in some embodiments. In a manner similar to the data storage device, the access key storage device 200 contains credential storage 232 for the provider's credentials. A controller 231 controls and supervises access to the provider credentials in provider credential storage by the data access device. The data access device communicates with the access keys storage device through electrical contacts 210 and/or an antenna 211.

Figure 3:
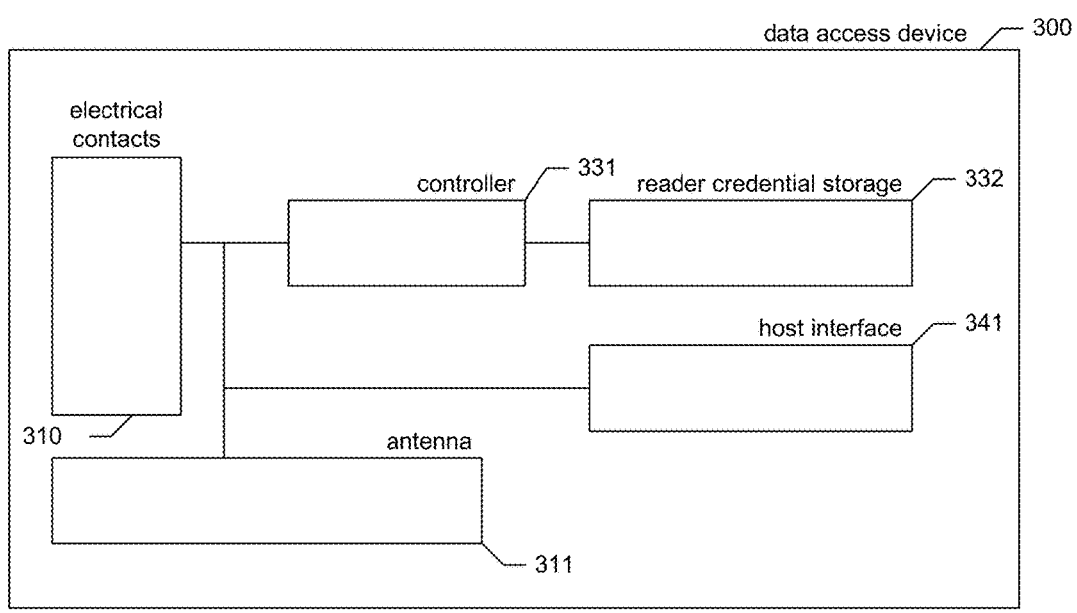
FIG. 3 is a device diagram showing a data access device used by the facility in some embodiments

FIG. 3 is a device diagram showing a data access device used by the facility in some embodiments. It can be seen that the data access device includes a host interface 341 connecting to a service provider computer system; electrical contacts 310 and/or an antenna 311 for communication with the data storage device and/or the access keys storage device; reader credential storage 322 for storing the data access device's credentials; and a controller 331 for managing interactions.

In some embodiments, the reader logs and signs any access to the data stored on the data storage device (both read and write, including the actual changes to the data) by the access key/signature stored securely on the access keys storage device.

In some embodiments, the data access device has a two-processor architecture to minimize any vulnerabilities related to its Data Encryption (or "Data Codec") Stack. The Data Processing Stack can be updateable (including, in some cases, remote updates) during the lifetime of the data access devices in order to support new and existing data formats and mappings, re-configure device-level processing algorithms and solutions including those for data filtering, setup particular aggregations, data abstractions and abstraction from personally identifiable information. On the other hand, the Data Codec Stack is protected from any changes or modifications as well as any attempts to extract the security data, information and algorithms from it; while the Data Processing Stack can be accessed, reconfigured and upgraded during the lifetime of the data access device, the Codec Stack is inaccessible after the initial initialization and virtually no information that may result in vulnerability can be extracted from it.

In some embodiments, the data access device performs hardware-level validation of the data and its format to ensure that only expected types of data are written and/or read from the data storage device, making it virtually impossible to share or distribute unauthorized data, viruses, etc.

Figure 4:
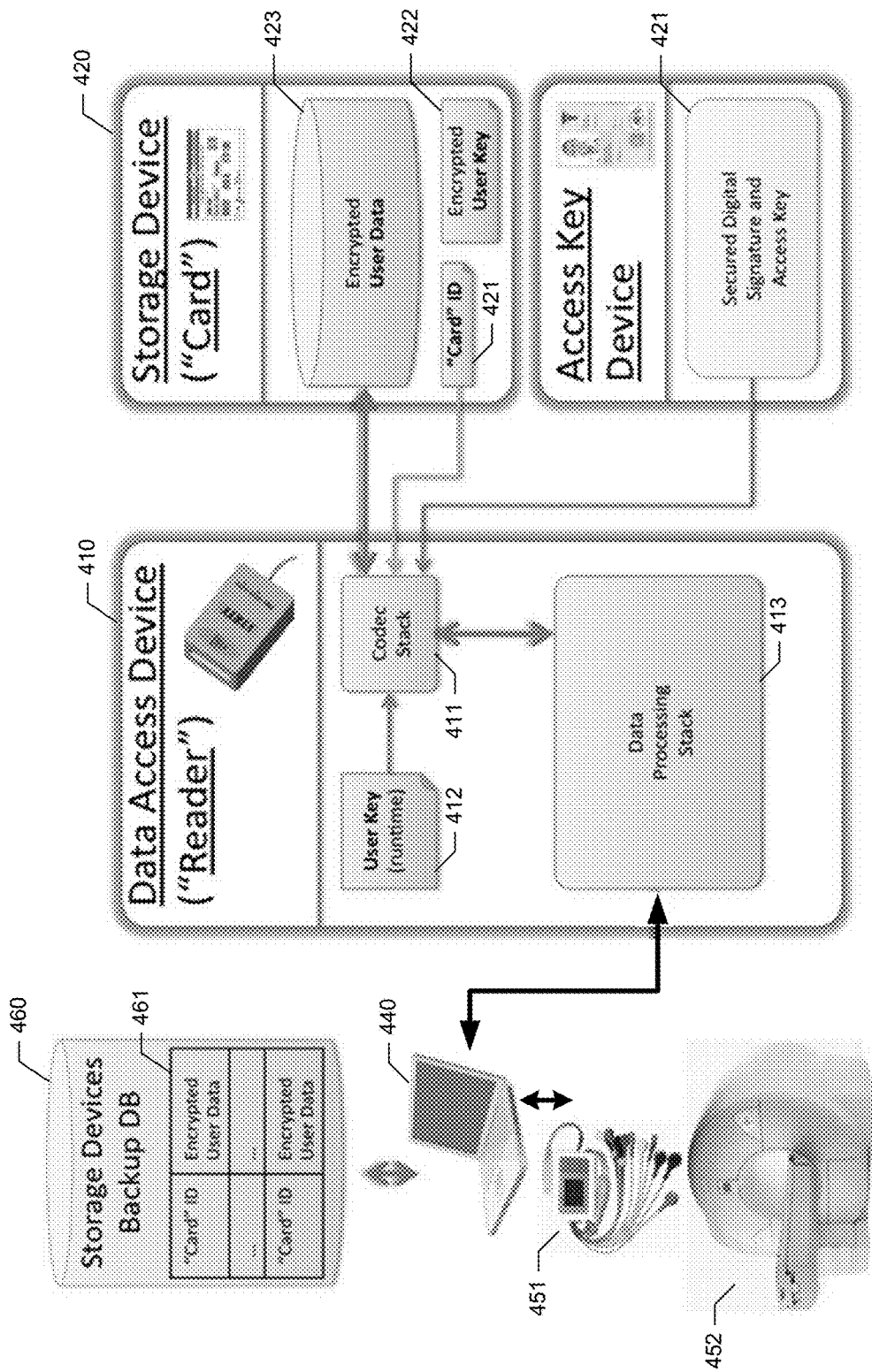
FIG. 4 is a data flow diagram showing data flow, data encryption and decryption, backup and data processing techniques used by the facility in some embodiments.

FIG. 4 is a data flow diagram showing data flow, data encryption and decryption, backup and data processing techniques used by the facility in some embodiments. It can be seen that a Codec Stack 411—the only physical place where User Data can be decrypted and encrypted—executes on a separate processor, which is physically isolated from application/processing parts of the data access device. The data access device also has a data processing stack 413 for interacting with a provider computer system 440, through which the reader can receive new health information, such as testing results from testing devices 451 and 452. As is discussed in greater detail below, through the provider computer system 440, the data processing stack can further submit encrypted individual information backups from the storage device that can be used if the storage device becomes lost or damaged to create the replacement. While the Data Processing Stack can be accessed, reconfigured and upgraded during the lifetime of the data access device, the Codec Stack is inaccessible after the initial initialization and virtually no information that may result in vulnerability can be pulled out of it.

Figure 5:
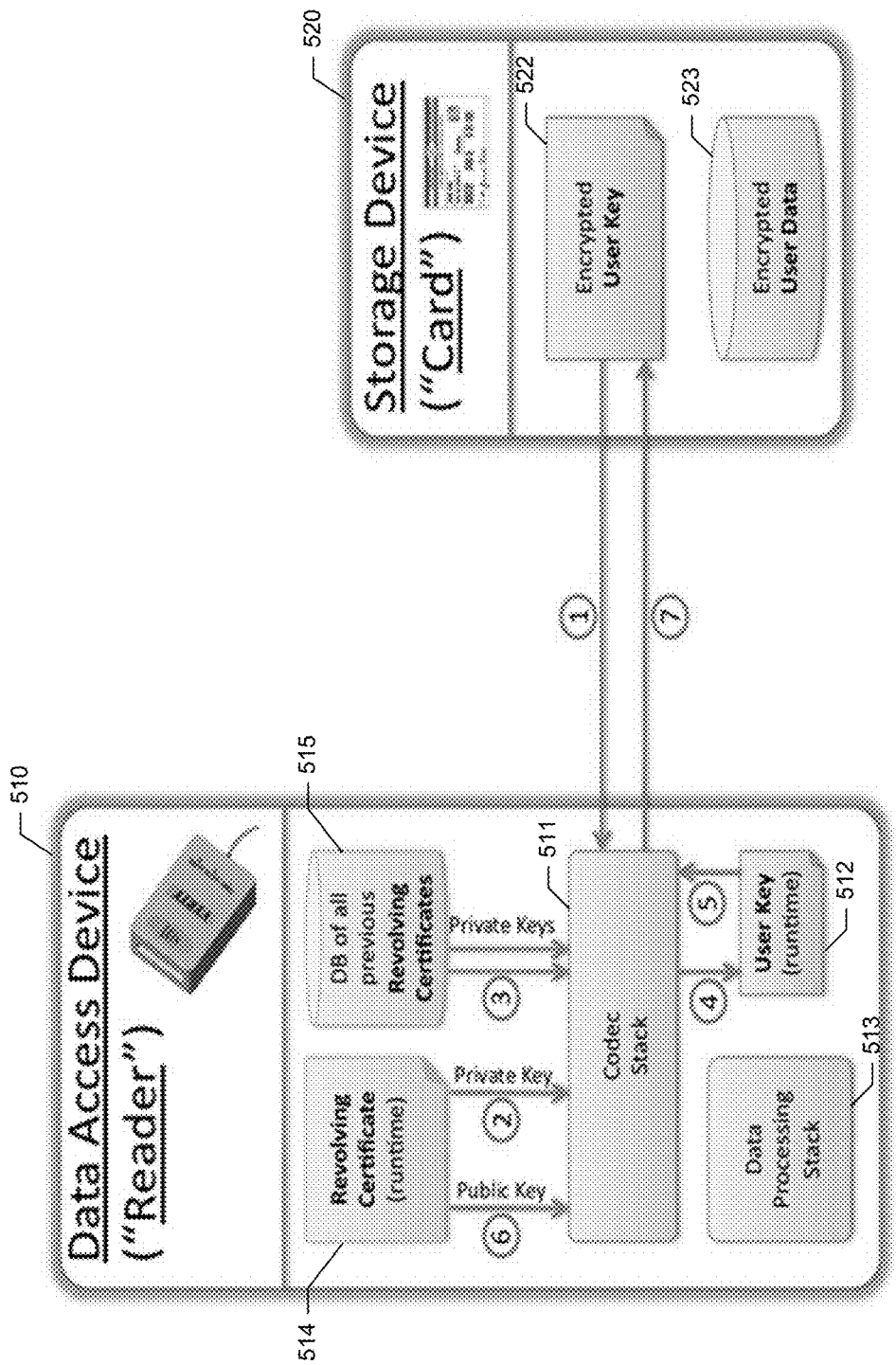
FIG. 5 is a data flow diagram showing a technique performed by the facility in some embodiments to reencrypt a data storage device's User Key with a newly updated Revolving Security/Encryption Certificate of the data access device.

FIG. 5 is a data flow diagram showing a technique performed by the facility in some embodiments to reencrypt a data storage device's User Key with a newly updated Revolving Security/Encryption Certificate of the data access device. The security certificate on the reader is issued by the health insurance company or another operating entity. This certificate is periodically renewed. Each time the patient's card is inserted into the data access device the card's security key is re-encrypted with the latest data access device's certificate. This way, readers that were de-certified by the operating entity lose the ability to decrypt card's key/certificate and use it to decrypt the actual payload. Since all the previous revolving certificates are stored on the data access device (in some embodiments in encrypted form), the data access device can decrypt the Encrypted User Key stored on the data storage device no matter how long ago the last access/re-encryption happened. Then the data access device re-encrypts the User Key with the most recent key and returns it back to the data storage device. This approach ensures that the data access devices that have not received the newest Revolving Certificate will lose the ability to access the data on the newly updated data storage devices.

In FIG. 5, Numbers in circles mark the sequence of steps in the data flow. In step 1, the data access device receives from the storage device the user key, encrypted with the latest revolving data access device certificate received by the data access device to write to the storage device. In step 2, the Codec Stack uses the private key of the latest revolving certificate received by the reader to attempt to decrypt the user key. If this is not successful, then in step 3, the Codec Stack repeats this process with each of the previously-received revolving certificates until the user key is decrypted. This produces, in step 4, a runtime copy 512 of the plain text user key. In steps 5 and 6, the Codec Stack uses the public key of the latest revolving certificate to reencrypt the plain text user key, and stores it in step 7 in the storage device in place of the former encrypted user key.

Figure 6:
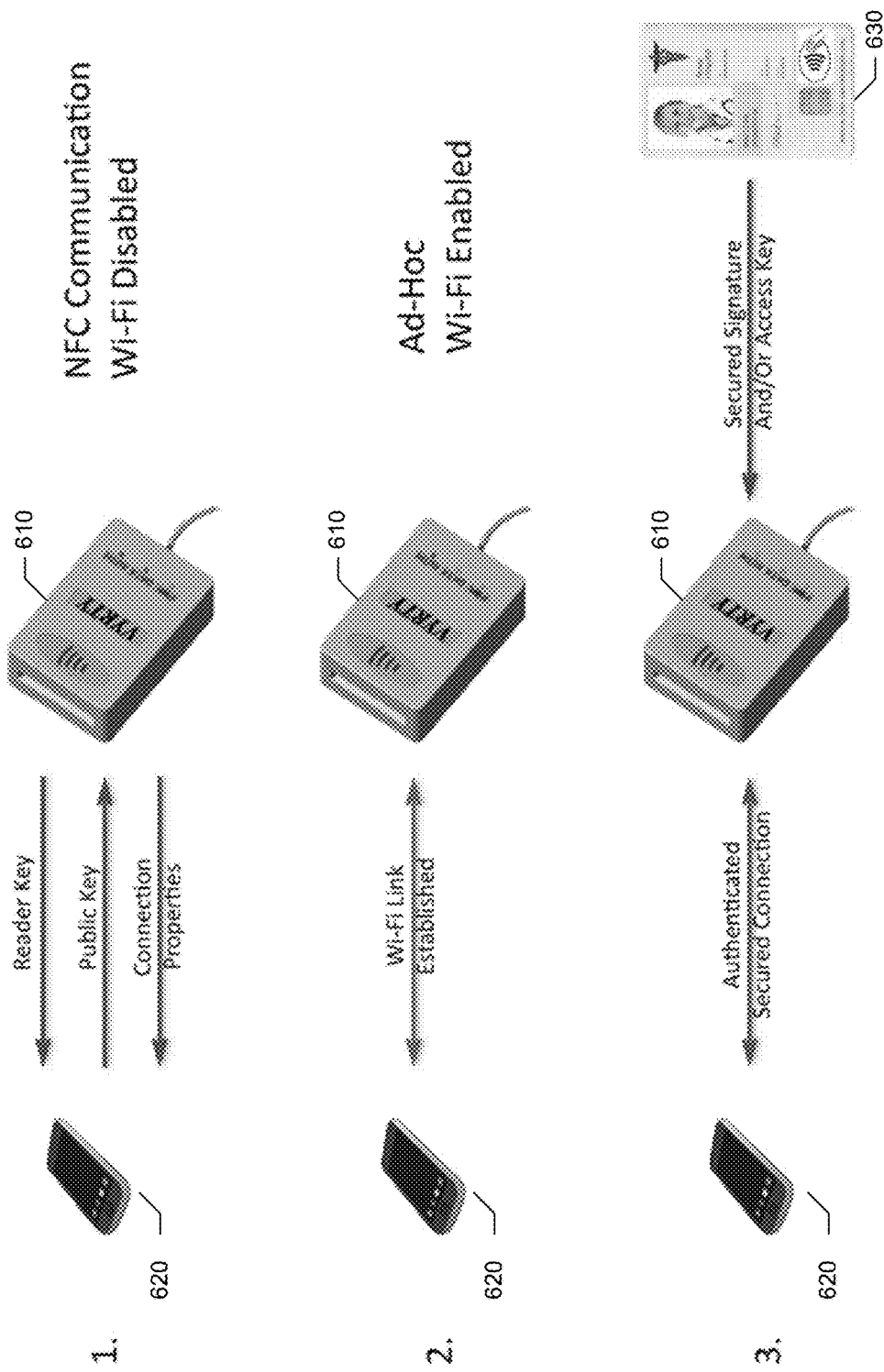
FIG. 6 is a data flow diagram showing a protocol used by the data access device to communicate with this smart phone in some embodiments.

In some embodiments, the user credentials and user's encrypted data are stored on a smart phone belonging to the user. FIG. 6 is a data flow diagram showing a protocol used by the data access device to communicate with this smart phone in some embodiments. During a first phase, the reader 610 disables WiFi communications and enables NFC communications. In this phase, the data access device 620 sends the cell phone a public key of the reader; the cell phone sends the data access device a public key of the user; and the data access device sends connection properties to the smart phone. In a second phase, the data access device turns on WiFi communications, and the smart phone uses the connection properties sent by the access device in the first phase in order to establish a WiFi connection with the access device. In some embodiments, before the smart phone provides the user's public key, or before the smart phone establishes the WiFi link, it explicitly seeks and obtains authorization from the user to connect with the access device. In a third phase, the access device uses the established WiFi connection in order to access the user's credentials and encrypted data on the smart phone. Also during this phase, the access device uses the user credentials together with credentials from the service provider 630 and credentials of the access device to decrypt, read, and write the user's encrypted data.

In various embodiments, the facility uses various other protocols to establish a secure, authenticated connection between the smart phone and the access device, using any of a variety of wireless communication techniques and authentication techniques, also including, for example, Bluetooth, and Internet access via a WiFi or cellular data connection.

Figure 7:
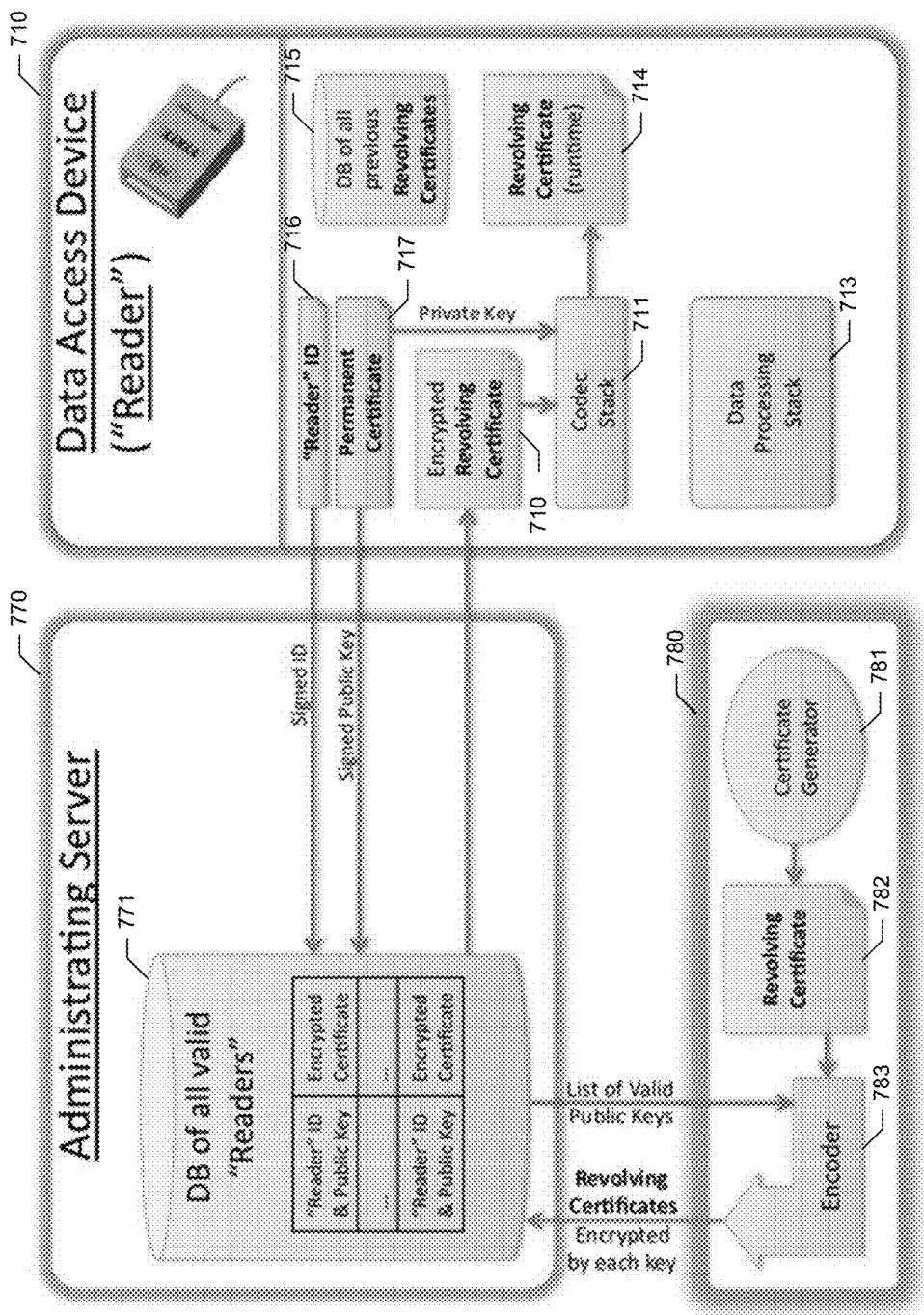
FIG. 7 is a data flow diagram showing a process used by the facility in some embodiments to periodically update the revolving security/encryption certificate on the data access device.

FIG. 7 is a data flow diagram showing a process used by the facility in some embodiments to periodically update the revolving security/encryption certificate on the data access device. The data access device re-encrypts each data storage device's User Key with the latest Revolving reader Certificate each time the data storage device is accessed.

In some embodiments, a certificate generator 781 that executes in an isolated offline environment periodically generates a new revolving certificate 782, such as monthly. Then an encoder 783, which runs in the same environment, encrypts this Security Certificate with the Public Key of each valid (and authorized) data access device 710 listed in reader database 771. The resulting list is stored on Administrating Servers 720, which are directly accessed by the data access devices to receive their copies of new revolving certificates. By removing a data access device from the database of valid readers, the facility prevents a removed data access device from being able to retrieve the current revolving certificate encrypted with its public key, i.e., encrypted in a way that it is able to decrypt with its private key.

A data access device maintains a local copy 715 of the list of all valid encryption/access keys (or certificates), or at least the unique IDs of those for the read-time validation of the changes made on the patient's card by other parties. In some embodiments, the governing (or administration) body of the particular organization maintains the database of all and each issued (and respectfully stored on each Physician's RFID card) encryption/access keys (or certificates). In some embodiments, each data access device periodically synchronizes with such central database.

In some embodiments, the data access device maintains whitelists and/or blacklists of keys or signatures for both users and service providers as a basis for controlling access to data storage device contents.

While FIG. 7 shows the Data Access Device sending a signed public key to the Administrating Server, in some embodiments the Data Access Device does not send a signed public key to the Administrating Server.

In some situations the data storage device can be disconnected or removed from the data access device before the new data record is completed and ready to be stored on the data storage device. In this case one or multiple online or otherwise connected storage devices, servers or services can be used for temporarily storing the new data (and complimenting data) that hasn't yet made its way to the data storage device.

Figure 8:
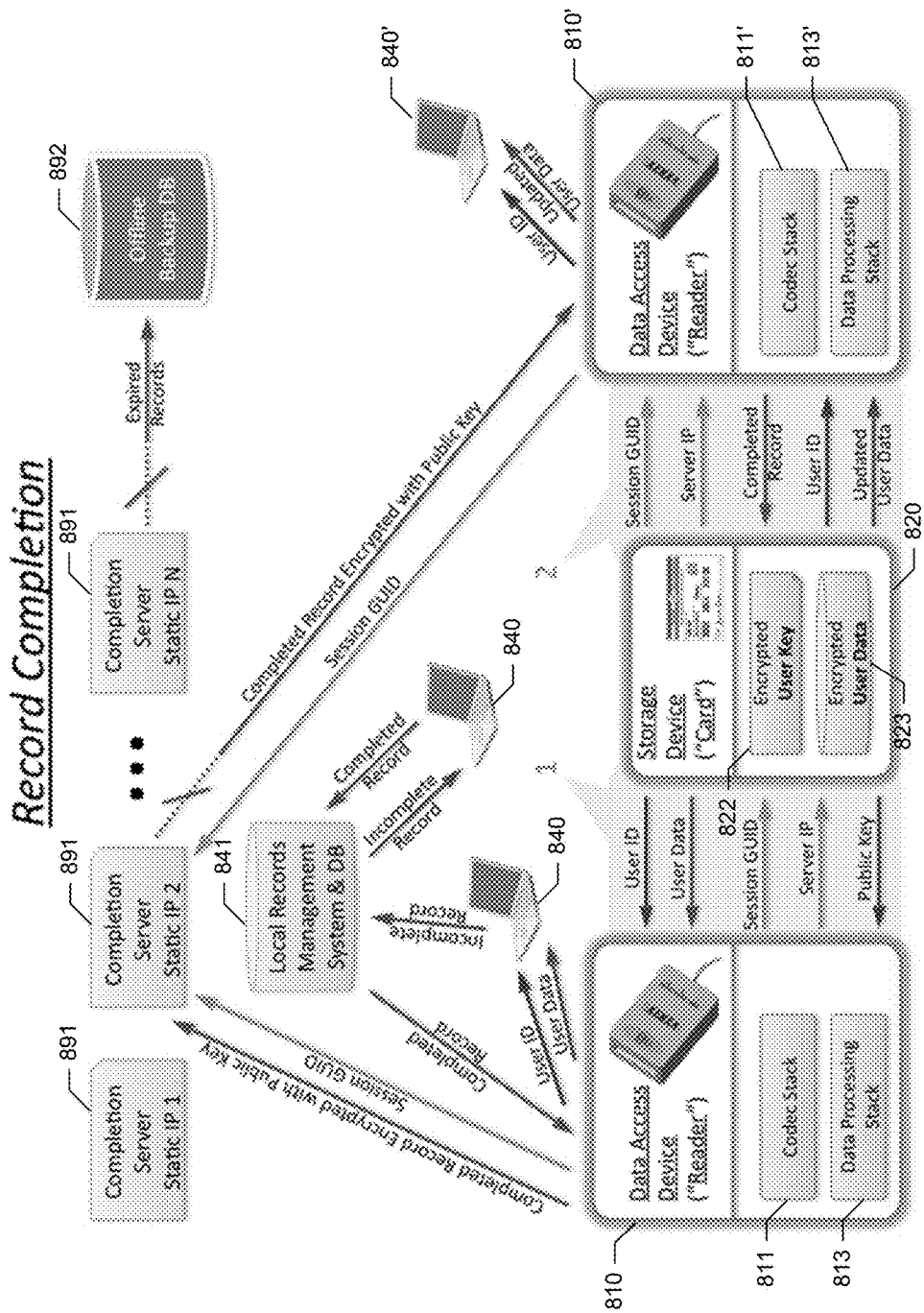
FIG. 8 is a data flow diagram showing a record completion process performed by the facility in some embodiments when the data storage device becomes disconnected, unplugged, or becomes otherwise inaccessible before a new data record is completed.

FIG. 8 is a data flow diagram showing a record completion process performed by the facility in some embodiments when the data storage device becomes disconnected, unplugged, or becomes otherwise inaccessible before a new data record is completed.

At a first stage (shown as highlighted area #1), the data storage device 820 is connected and communicating with a first data access device 810. "User ID" and "User Data" (which may be empty, or may contain previous data records) are accessed and decrypted by the data access device. The first data access device generates a "Session GUID" identifying a record completion session and stores it on the data access device. The first data access device requests the "public" part of the asymmetrical security certificate of the data storage device and temporarily caches it inside own memory. In some embodiments, the expiration of such cache is configurable. The first data access device allows the connected PC, Tablet or another type of connected provider computer or device 840 to access "User ID" and "User Data" in order to initiate a new data record. The first data access device randomly (or according to some set of rules) selects the Static IP address (or other identification) of the server, service, or device 891 it is planning to use for the temporary data record storage. The data access device stores this IP address or another identification on the data storage device. At this or later stage (potentially before the new data record is completed), the data storage device is disconnected from the data access device and becomes therefore inaccessible to the first data access device. The new data record gets completed on the same computer or device to which the data access device is connected, or on another device or computer (in the situation where data records are managed from and by a local records management system and are getting stored in the respective DB). The data access device (having ways to communicate with the computer or the DB containing the new data records) detects (through a particular pull or push protocol) that the record is ready. In some embodiments, it need not be absolutely finished at this stage, but it is in a usable form in accordance with a particular set of definitions. In some embodiments, record completion can be initiated manually; for example, a service provider can use his or her computer to explicitly notify the data access device when a record is complete. The data access device encrypts the new data record with the "public" key previously cached from the presently inaccessible data storage device. The data access device sends the encrypted new record for temporary storage on the previously selected server, service, or device.

In a second stage (shown as highlighted area #2), the data storage device is connected to the same or a different data access device 810'. At this stage, the data access device detects one or more "Session ID's" each identifying a data record that was not yet complete at the last time the data storage device was communicating with any data access device. Each such data record may now be complete, or may still be incomplete. The data access device then pulls the corresponding "Server IP address" (or other identification) of the server, service, or device the respective record was originally stored on, establishes an appropriate connection, and downloads the previously stored encrypted data record. The data access device updates the user data on the data storage device with the new data record. The data access device pulls the "User ID" and the "User Data" updated with the new data record from the data storage device, then decrypts it and verifies its validity and integrity. Once confirmed, the data access device sends the confirmation to the server, service, or device (that was used as a temporary storage) requesting this data record be deleted and cleans up the records on the data storage device. Where the data record is not requested from the temporary storage location within the predefined expiration period, it can be sent to an offline storage/backup location and deleted from the temporary storage. In some embodiments, the facility randomly selects a server from the collection of servers for the temporary storage of the data record. In some embodiments, the facility randomly selects a service from the collection of services for the temporary storage of the data record. In some embodiments, the facility randomly selects a device from the collection of devices for the temporary storage of the data record. In some embodiments, the facility uses temporary storage (servers, services, or storage devices) for storing only a delta or difference between the data that was already stored on the data storage device at the time it was disconnected or became otherwise inaccessible and the completion (by the variety of definitions) of the corresponding record. In some embodiments, the facility uses pairs of randomly selected server, service or device identification and randomly generated "Session ID" for finding the respective record.

In some embodiments, the facility deletes the record after the respective "User Data" is confirmed correctly updated. In some embodiments, the facility uses asymmetrical encryption approaches for delta (difference in data records) encryption for the temporary storage of such data record. In some embodiments, the facility accesses the new data record only as a part of the "User Data" only from the data storage device only after it's updated with the new data record. This means that the data record that was downloaded from the temporary storage is meaningless by itself; it cannot be decrypted or otherwise used as a standalone record.

Figure 9:
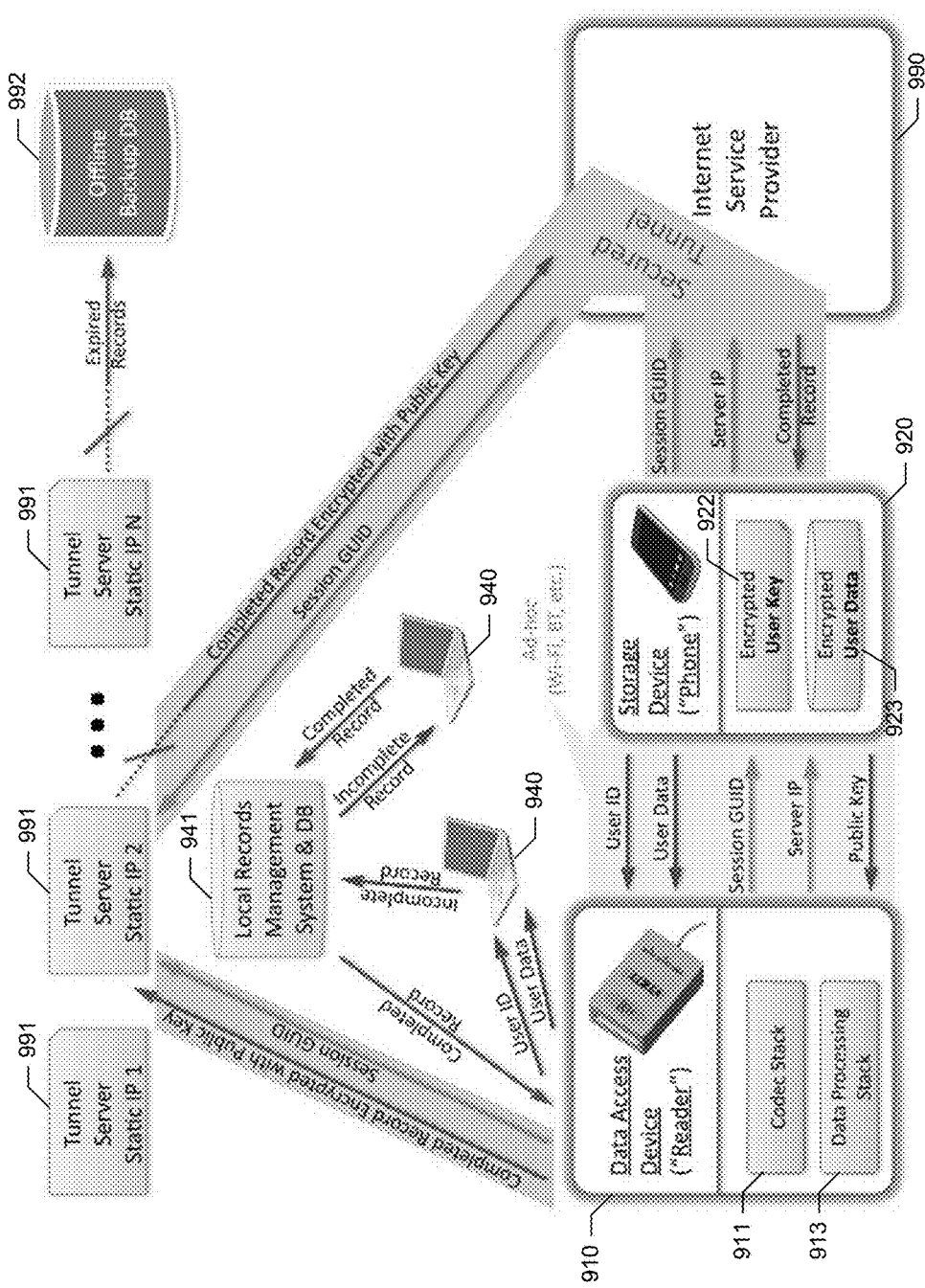
FIG. 9 is similar to FIG. 8 discussed above, and shows the record completion process where a user's smart phone 920 is used to store the user's credentials and encrypted data.

FIG. 9 is similar to FIG. 8 discussed above, and shows the record completion process where a user's smart phone 920 is used to store the user's credentials and encrypted data. The technique is similar to that shown in FIG. 8, except that the smart phone uses its own capability 990 to access the Internet—e.g., via a WiFi or cellular data connection—to communicate directly with the completion server that was selected for the incomplete record, via a secured tunnel.

Figure 10:
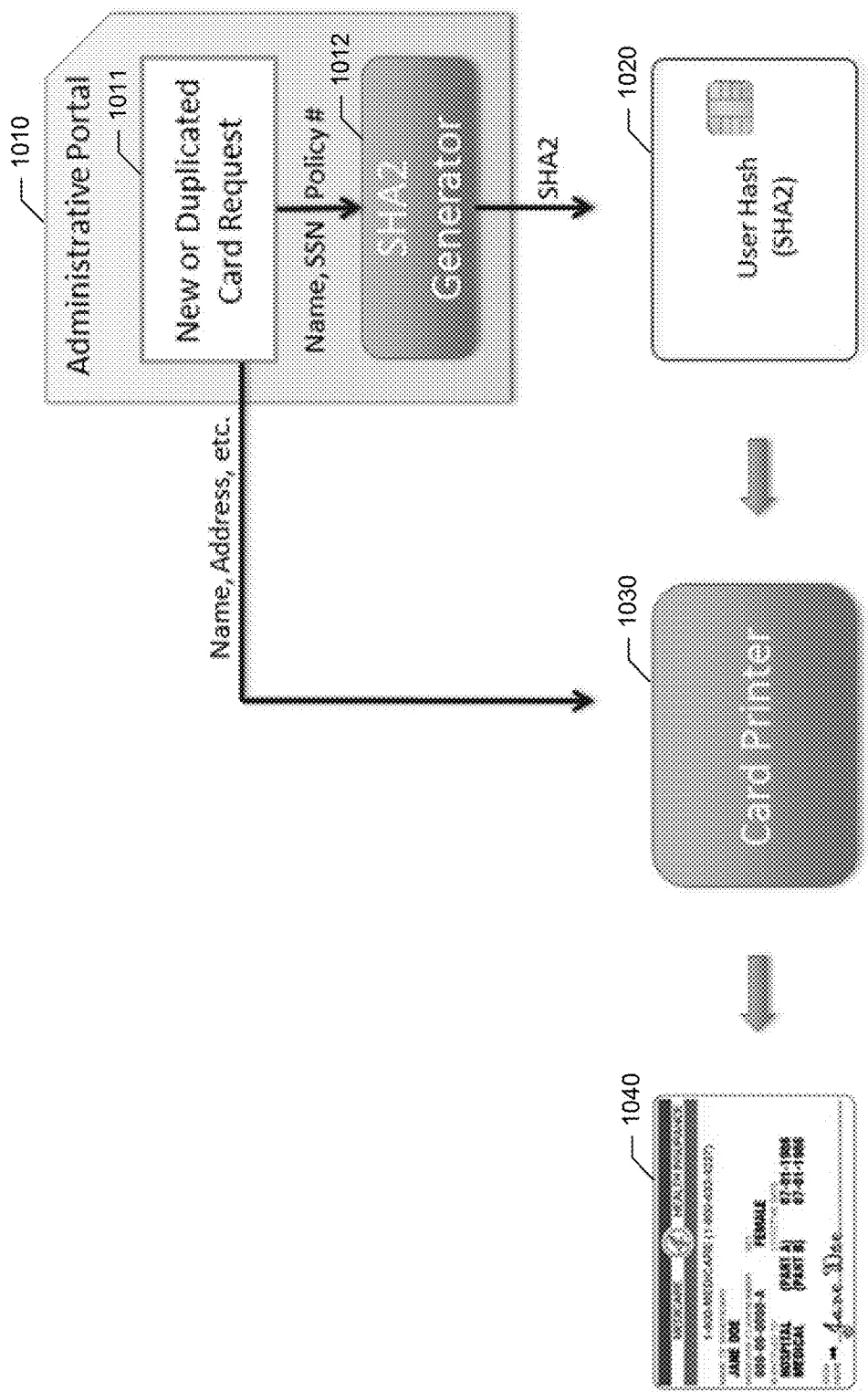
FIG. 10 is a flow diagram that shows a first stage of a card generation process performed by the facility in some embodiments.

FIG. 10 is a flow diagram that shows a first stage of a card generation process performed by the facility in some embodiments. In an Administrative Portal 1010, an administrative user enters a card request 1011 including parameters of a new or existing user for which a card is to be created. These parameters are typically invariant with respect to the user, such as Name, Gender, DOB, etc. This occurs both when the facility is generating the first data storage device for a user, and where the facility is generating a subsequent data storage device for the user to replace a lost or damaged data storage device of the user. The facility uses a hashing generator 1012 to generate a unique hash for the user (for example, a SHA2 or MD5 hash) based on the user parameters. The facility copies the unique user hash onto a blank Card 1020. The user parameters are used by a Card Printer 1030 to print human-readable information on the Card, such as user name, sex, identification number, coverage details, signature, etc. Now the Card 1040 is ready to be initialized with the Card Certificate.

Figure 11:
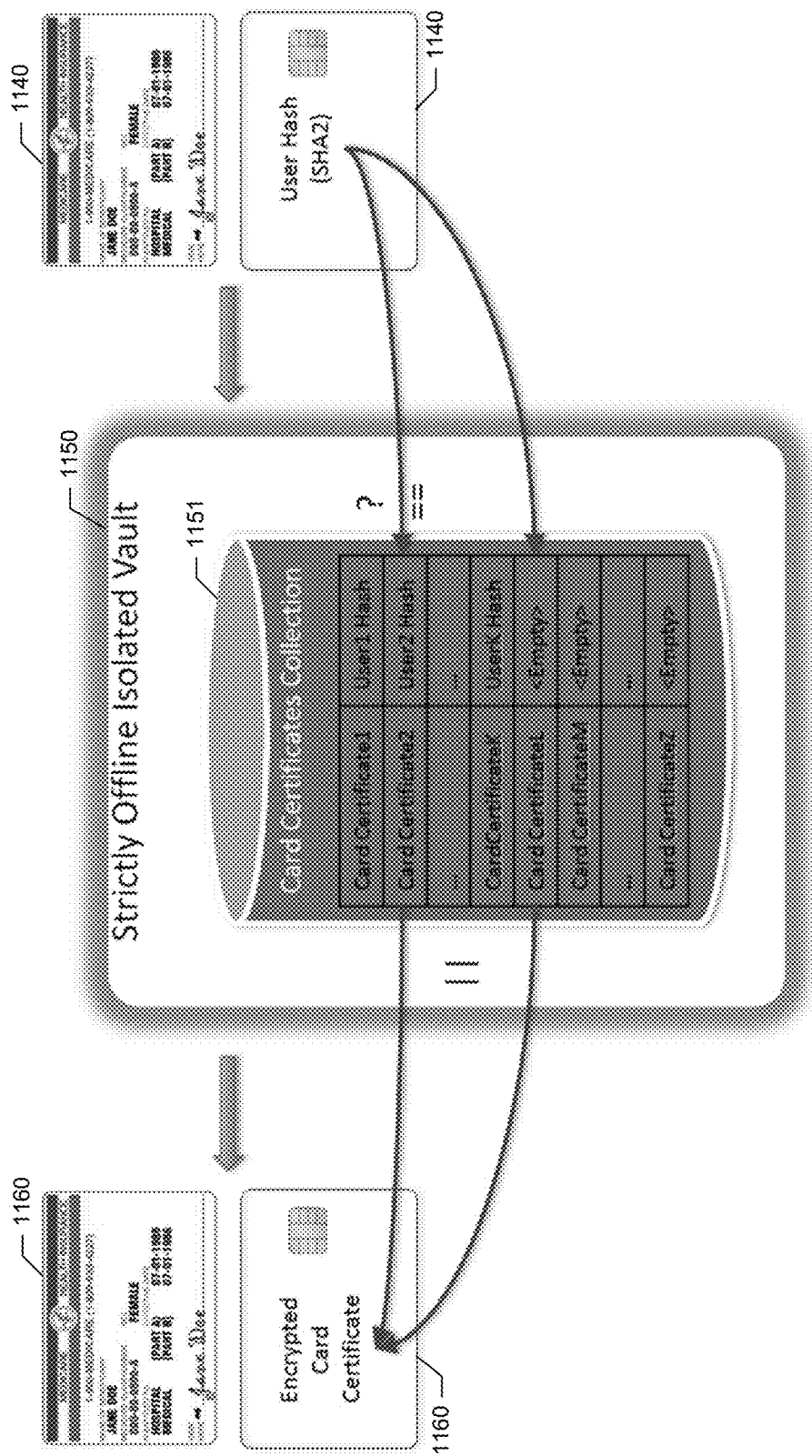
FIG. 11 is a flow diagram that shows a second stage of the card generation process performed by the facility in some embodiments.

FIG. 11 is a flow diagram that shows a second stage of the card generation process performed by the facility in some embodiments. A Card Certificates Collection 1151 is a database that is initialized once with a very large number of randomly generated Card Certificates, such as one billion, each encrypted using an initial Reader Certificate. In some embodiments, the card certificates collection is stored in a physically and communicatively isolated vault 1150 into which no wired or wireless network connections pass. The new Card 1140 containing a User Hash identifying the user is connected to the Card Certificates Collection. In some embodiments, the user hash is a hash value generated by performing a consistent hashing algorithm against identifying information for the user, such as social security number, normalized name, etc. In some embodiments, the user hash is an arbitrary identifier for the user that is otherwise mapped to from identifying information for the user. If this User Hash already exists in the DB (meaning we are restoring lost/stolen/damaged Card), then the facility copies the corresponding encrypted Card Certificate onto the Card. Now this Card is ready for User Payload Data to be restored from the Backup DB. If this User Hash cannot be found, meaning that it is a new User, then the facility copies the User Hash to the next "Empty" slot of the DB, and copies the corresponding Card Certificate onto the Card. Now the Card 1160 is ready to be securely conveyed to the User, such as via trackable mail, in person pick-up, etc.

Figure 12:
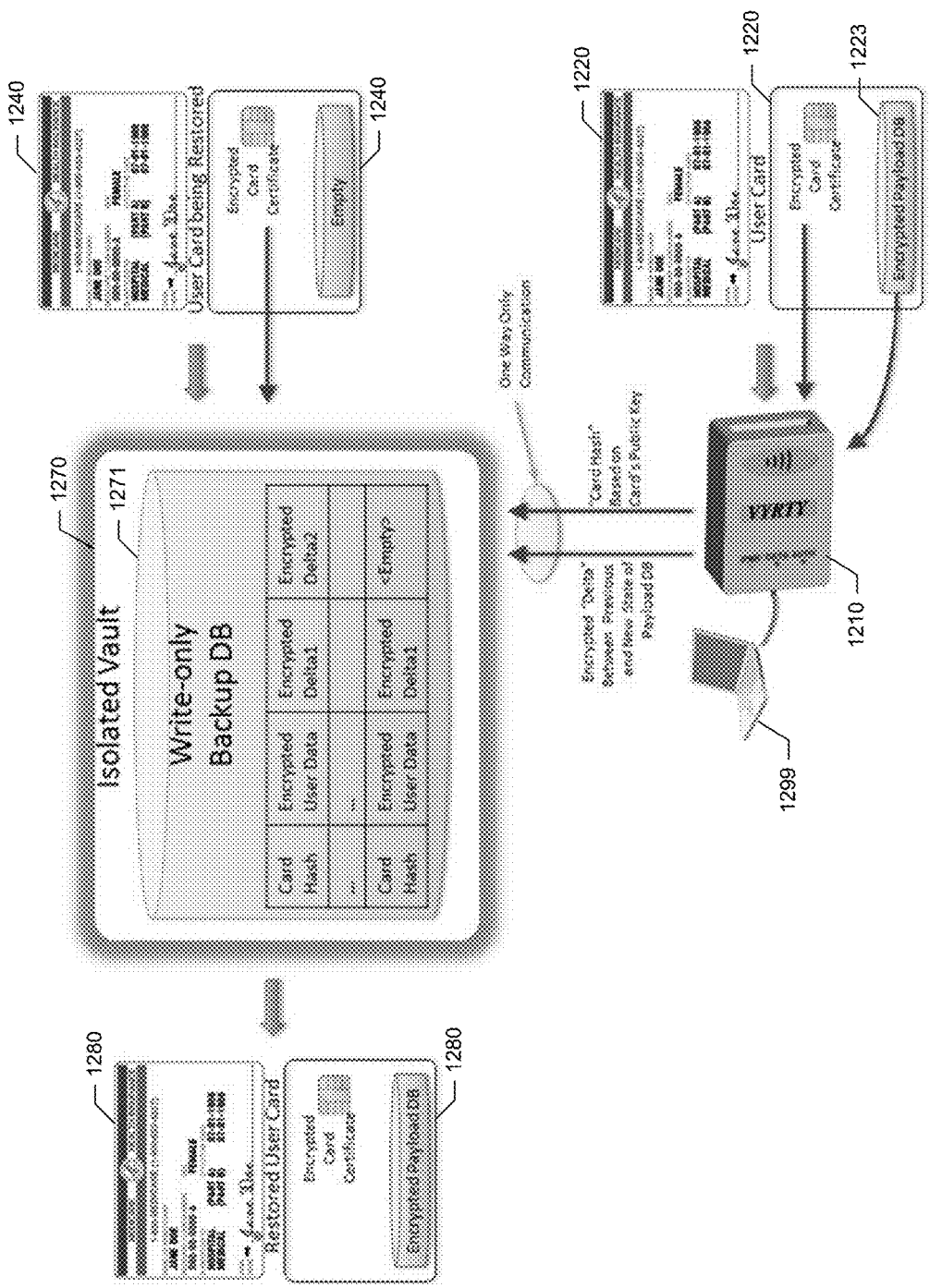
FIG. 12 is a data flow diagram showing a backup operation performed by the facility in some embodiments to be able to replace the contents of a lost or damaged data storage device.

FIG. 12 is a data flow diagram showing a backup operation performed by the facility in some embodiments to be able to replace the contents of a lost or damaged data storage device. After the reader performs each Payload DB update on the Card 1220, the Reader 1210 encrypts the Delta (difference) between the new state and the previous state of the Payload DB 1223 using Card's Public Key and sends it to the Backup DB 1271 in an isolated vault 1270 together with the Card Hash generated based on the same Public Key via a "One Way" type of communication channel. For example, in some embodiments, to implement one-way communication, the facility uses an optical communication link in which the receiving end has an optical sensor, and only the transmitting end has a light emitter. Only the encrypted and de-identified data payload can be copied from the card for the backup processes; the key/certificate and anything related to personally identifiable information cannot be extracted from the card. In some embodiments, the backup server signs backup copies for guaranteed verification/validation of backup transactions. This way data that is restored from the backup can be verified for validity. In some embodiments, a delete operation can only occur on the Patient's Card if online backup of the respective files has succeeded. The backup server confirms backup transaction by returning encrypted and signed confirmation.

For restoration from the Backup DB, a new Card 1240 with the same Card Security Certificate is used. A Card Hash is generated from the Public Key of the new Card using the same hashing algorithm. Where the Card Hash matches the existing entry, the encrypted Payload entries are copied on the Card. The Card 1280 now is ready to be securely transported to the User.

Figure 13:
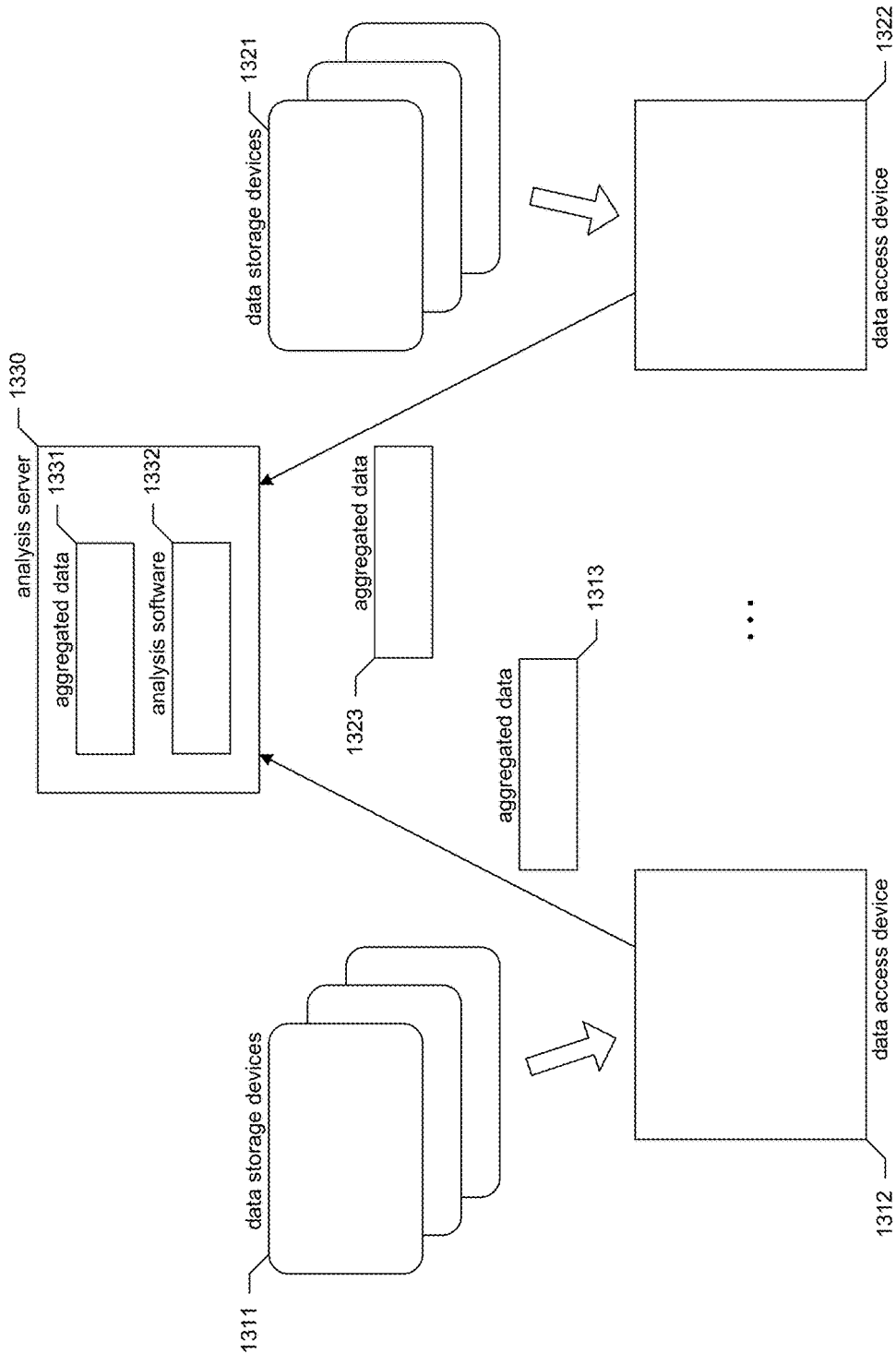
FIG. 13 is a data flow diagram showing an aggregate data analysis process performed by the facility in some embodiments.

FIG. 13 is a data flow diagram showing an aggregate data analysis process performed by the facility in some embodiments. For example, in some embodiments, the facility performs data analysis to discern health and/or treatment trends among patients using the facility. In this data flow, a data access device such as data access device 1312 aggregates certain data from among the data storage devices 1311 with which it interacts. Periodically, the data access device sends this aggregated data 1313 to an analysis server 1330. In some embodiments, there's a lower limit on the number of patients whose data can be incorporated in a batch of aggregated data 1313 sent to the analysis server, such as 10 patients. In the analysis server, the facility collects the aggregated data 1331 from across multiple data access devices, subjects it to analysis techniques implemented by analysis software 1332.

Figure 14:
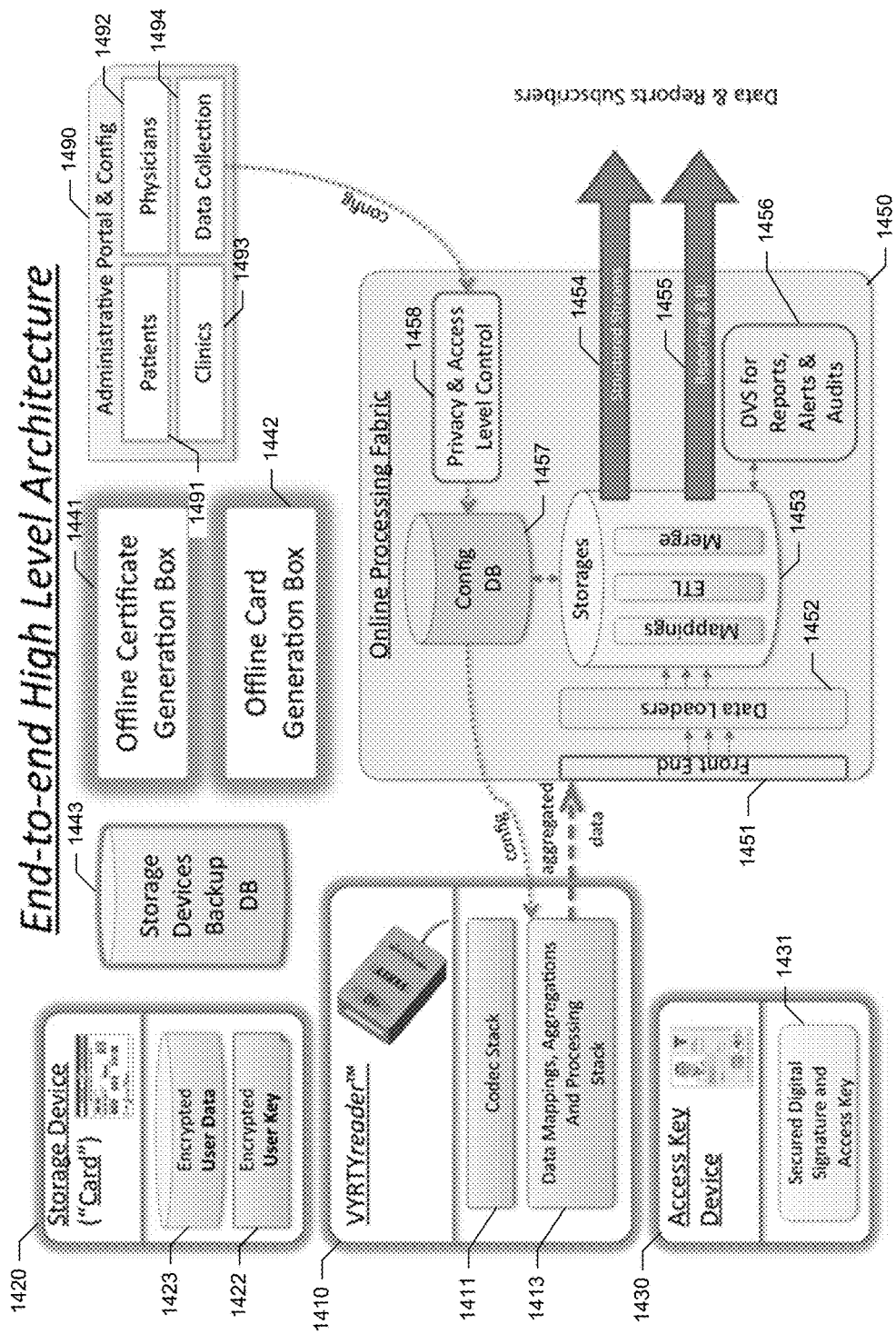
FIG. 14 shows an end-to-end high-level architecture employed by the facility in some embodiments.

FIG. 14 shows an end-to-end high-level architecture employed by the facility in some embodiments. It can be seen that de-identified, aggregated, statistical, and instrumentation data is sent to an online processing fabric for further consumption.

Figure 15:
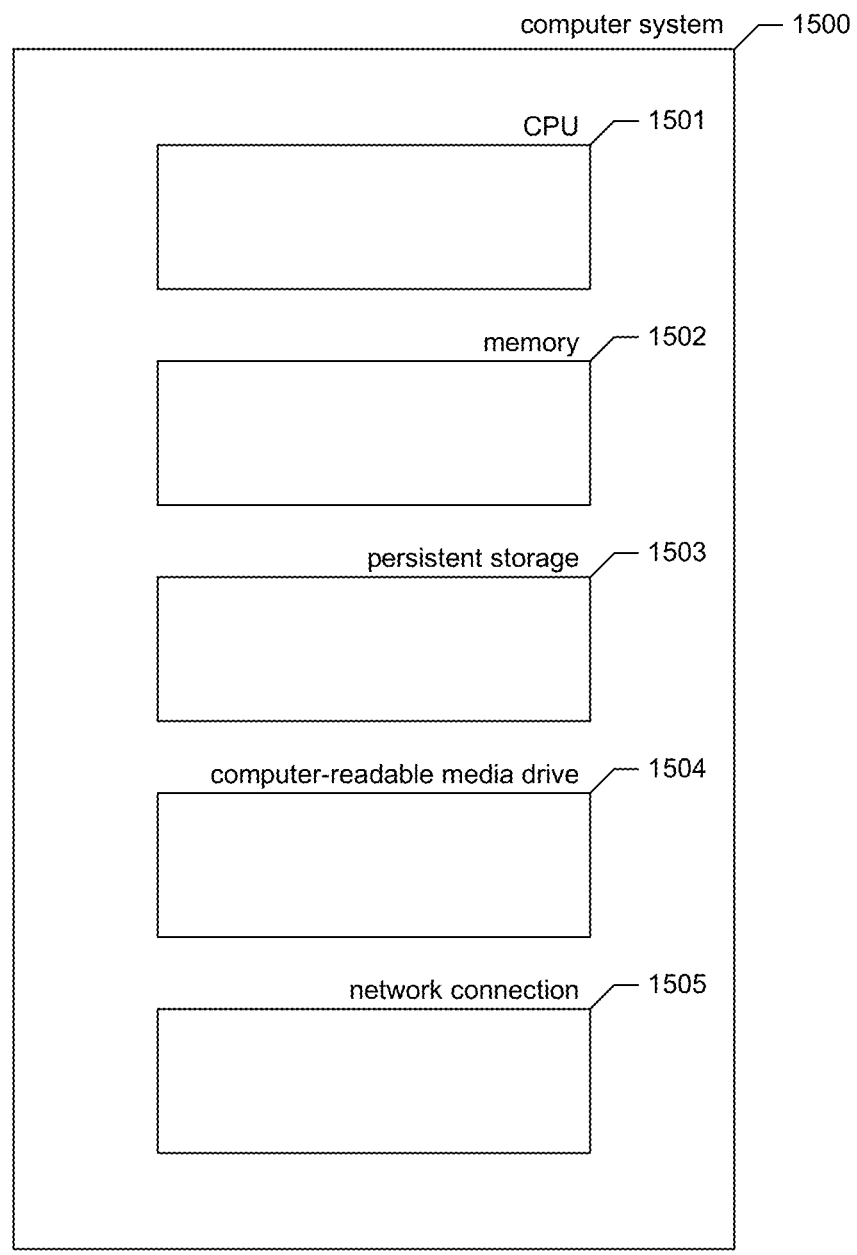
FIG. 15 is a block diagram showing some of the components typically incorporated in at least some of the computer systems and other devices on which the facility operates.

FIG. 15 is a block diagram showing some of the components typically incorporated in at least some of the computer systems and other devices on which the facility operates. In various embodiments, these computer systems and other devices 1500 can include server computer systems, desktop computer systems, laptop computer systems, mobile phones, personal digital assistants, televisions, cameras, automobile computers, electronic media players, etc. In various embodiments, the computer systems and devices include zero or more of each of the following: a central processing unit ("CPU") 1501 for executing computer programs; a computer memory 1502 for storing programs and data while they are being used; a persistent storage device 1503, such as a hard drive or flash drive for persistently storing programs and data; a computer-readable media drive 1504, such as a floppy, CD-ROM, or DVD drive, for reading programs and data stored on a computer-readable medium; and a network connection 1505 for connecting the computer system to other computer systems to send and/or receive data, such as via the Internet or another network and its networking hardware. While computer systems configured as described above are typically used to support the operation of the facility, those skilled in the art will appreciate that the facility may be implemented using devices of various types and configurations, and having various components.

In some embodiments, the facility stores individual information of a variety of types. For example, in some embodiments, the facility stores individual information relevant to financial services. In various embodiments, such information can include social security numbers and other identifying information, credit score, employment history, account numbers and balances, information about financial instruments and other property presently or formally owned and its value at various times, investment strategies and histories, etc. In some such embodiments, data access devices are provided to service providers such as bank branches, investment advisors, employers, loan underwriters, retirement and other financial planners, etc.

In some embodiments, the facility stores individual information comprises travelling information. In a variety of such embodiments, such information can include traveler identification information, traveler citizenship information, traveler residency status, information regarding government-issued travel documents such as passports and visas, travel history, photographs, licensure for automobile driving and other forms of vehicle control, etc. In some such embodiments, data access devices are provided to customs and border patrol agents, government passport and visa authorities, travel agents, airlines and other travel providers, etc.

In some embodiments, the facility stores individual information relating to education, training, and/or profession certification. In a variety of such embodiments, the individual information includes educational information regarding institution, classes, grades, instructors and educational facilities, admissions examinations, completion examinations, degrees conferred, professional certifications and their statuses, etc. In some such embodiments, data access devices are provided to educational institutions and instructors, professional certification authorities, employers, etc.

It will be appreciated by those skilled in the art that the above-described facility may be straightforwardly adapted or extended in various ways.

We claim:

1. A method of one or more computing devices for targeting individual information to a storage device, comprising:
   at a time when the storage device is accessible by a first computing device, in the first computing device:
   (a) causing to be stored in the storage device an identifier of individual information;
   at a time when the storage device is not accessible by the first computing device, in the first computing device:
   (b) obtaining the individual information;
   (c) encrypting the individual information with a public key associated with the storage device;
   (d) causing the encrypted individual information to be stored in an Internet-connected server in connection with the individual information identifier;
   at a time when the storage device is accessible by a second computing device, in the second computing device:
   (e) causing the individual information identifier to be retrieved from the storage device;
   (f) using the retrieved individual information identifier to retrieve the encrypted individual information from the server; and
   (g) causing to be stored in the storage device the retrieved encrypted individual information.

2. The method of claim 1 wherein the first and second computing devices are the same computing device.

3. The method of claim 1 wherein the first and second computing devices are different computing devices.

4. The method of claim 1 wherein (e) is performed in response to the storage device becoming accessible by the second computing device.

5. A computer-readable medium having contents configured to cause, when executed by a processor, one or more computing devices to perform a method for targeting individual information to a storage device, the computer-readable medium not being a signal, the method comprising:
   at a time when the storage device is accessible by a first computing device, in the first computing device:
   (a) causing to be stored in the storage device an identifier of individual information;
   at a time when the storage device is not accessible by a first computing device, in the first computing device:
   (b) obtaining the individual information;
   (c) encrypting the individual information with a public key associated with the storage device;
   (d) causing the encrypted individual information to be stored in an Internet-connected server in connection with an identifier stored in the storage device;
   at a time when the storage device is accessible by a second computing device, in the second computing device:
   (e) causing the identifier to be retrieved from the storage device;
   (f) using the retrieved identifier to retrieve the encrypted individual information from the server; and
   (g) causing to be stored in the storage device the retrieved encrypted individual information.

6. The computer-readable medium of claim 5 wherein the first and second computing devices are the same computing device.

7. The computer-readable medium of claim 5 wherein the first and second computing devices are different computing devices.

8. The computer-readable medium of claim 5 wherein (e)-(g) are performed in response to the storage device becoming accessible by the second computing device.

9. The computer-readable medium of claim 5, the method further comprising:
   at a time when the storage device is accessible by the first computing device, in the first computing device:
   causing to be stored in the storage device information identifying the server,
   and wherein (f) uses the information identifying the server stored in the storage device.

10. A computing system configured to target individual information to a storage device, comprising:
    a first computing device, configured to:
    at a time when the storage device is accessible by the first computing device:
    (a) cause to be stored in the storage device an identifier of individual information and information identifying an Internet-connected server;
    at a time when the storage device is not accessible by the first computing device:
    (b) obtain the individual information;
    (c) encrypt the individual information with a public key associated with the storage device; and
    (d) cause the encrypted individual information to be stored in an Internet-connected server in connection with an identifier stored in the storage device; and
    a second computing device, configured to:
    at a time when the storage device is accessible by the second computing device:
    (e) cause the identifier to be retrieved from the storage device;
    (f) use the retrieved identifier to retrieve the encrypted individual information from the server; and
    (g) cause to be stored in the storage device the retrieved encrypted individual information.

11. The computing system of claim 10 wherein the first and second computing devices are the same computing device.

12. The computing system of claim 10 wherein the first and second computing devices are different computing devices.

13. The computing system of claim 10 wherein the second computing device is configured to perform (e) in response to the storage device becoming accessible by the second computing device.

14. The computing system of claim 10, the first computing device further configured to:
  at a time when the storage device is accessible by the first computing device:
  cause to be stored in the storage device information identifying the server,
  and wherein (f) uses the information identifying the server stored in the storage device.

15. A method of one or more computing devices for targeting individual information to a storage device, comprising:
  at a time when the storage device is not accessible by a first computing device, in the first computing device:
  (a) obtaining the individual information;
  (b) encrypting the individual information with a public key associated with the storage device;
  (c) causing the encrypted individual information to be stored in an Internet-connected server in connection with an individual information identifier;
  at a time when the storage device is accessible by a second computing device, in the second computing device:
  (d) causing the individual information identifier to be retrieved from the storage device;
  (e) using the retrieved individual information identifier to retrieve the encrypted individual information from the server;
  (f) causing to be stored in the storage device the retrieved encrypted individual information; and
  (g) causing to be stored in the storage device information identifying the server,
  and wherein (e) uses the information identifying the server stored in the storage device.

16. The method of claim 15 wherein the first and second computing devices are the same computing device.

17. The method of claim 15 wherein the first and second computing devices are different computing devices.

18. The method of claim 15 wherein (e) is performed in response to the storage device becoming accessible by the second computing device.

19. A computer-readable medium having contents configured to cause, when executed by a processor, one or more computing devices to perform a method for targeting individual information to a storage device, the computer-readable medium not being a signal, the method comprising:
  at a time when the storage device is not accessible by a first computing device, in the first computing device:
  (a) obtaining the individual information;
  (b) encrypting the individual information with a public key associated with the storage device;
  (c) causing the encrypted individual information to be stored in an Internet-connected server in connection with an identifier stored in the storage device;
  at a time when the storage device is accessible by a second computing device, in the second computing device:
  (d) causing the identifier to be retrieved from the storage device;
  (e) using the retrieved identifier to retrieve the encrypted individual information from the server;
  (f) causing to be stored in the storage device the retrieved encrypted individual information; and
  (g) causing to be stored in the storage device information identifying the server,
  and wherein (e) uses the information identifying the server stored in the storage device.

20. The computer-readable medium of claim 19 wherein the first and second computing devices are the same computing device.

21. The computer-readable medium of claim 19 wherein the first and second computing devices are different computing devices.

22. The computer-readable medium of claim 19 wherein (d)-(f) are performed in response to the storage device becoming accessible by the second computing device.

23. A computing system configured to target individual information to a storage device, comprising:
  a first computing device, configured to:
  at a time when the storage device is not accessible by the first computing device:
  (a) obtain the individual information;
  (b) encrypt the individual information with a public key associated with the storage device; and
  (c) cause the encrypted individual information to be stored in an Internet-connected server in connection with an identifier stored in the storage device;
  a second computing device, configured to:
  (d) cause the identifier to be retrieved from the storage device;
  (e) use the retrieved identifier to retrieve the encrypted individual information from the server; and
  (f) cause to be stored in the storage device the retrieved encrypted individual information; and
  a third computing device, configured to:
  (g) cause to be stored in the storage device information identifying the server,
  and wherein (e) uses the information identifying the server stored in the storage device.

24. The computing system of claim 23 wherein the first and second computing devices are the same computing device.

25. The computing system of claim 23 wherein the first and second computing devices are different computing devices.

26. The computing system of claim 23 wherein the second computing device is configured to perform (e) in response to the storage device becoming accessible by the second computing device.

* * * * *